(12) United States Patent
Tonomura et al.

(10) Patent No.: US 9,416,147 B2
(45) Date of Patent: Aug. 16, 2016

(54) PREPARATION OF SILAZANE COMPOUND

(71) Applicant: Shin-Etsu Chemical Co., Ltd., Tokyo (JP)

(72) Inventors: Yoichi Tonomura, Joetsu (JP); Tohru Kubota, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/665,093

(22) Filed: Mar. 23, 2015

(65) Prior Publication Data

US 2015/0284414 A1  Oct. 8, 2015

(30) Foreign Application Priority Data

Apr. 3, 2014  (JP) .................................. 2014-076769

(51) Int. Cl.
    *C07F 7/02* (2006.01)
    *C07F 7/10* (2006.01)
    *C09D 4/00* (2006.01)

(52) U.S. Cl.
    CPC ...... *C07F 7/10* (2013.01); *C09D 4/00* (2013.01)

(58) Field of Classification Search
    CPC .................................... C07F 7/10; C09D 4/00
    USPC .......................................................... 556/412
    See application file for complete search history.

(56) References Cited

U.S. PATENT DOCUMENTS 2,429,883 A    10/1947    Johannson
6,329,487 B1 *  12/2001    Abel et al. ...................... 528/21

FOREIGN PATENT DOCUMENTS

| GB | 1 516 899 |   | 7/1978  |                |
|----|-----------|---|---------|----------------|
| GB | 1516899 A | * | 7/1978  | ........ C07F 7/10 |
| GB | 1526899 A | * | 10/1978 | ........ C23C 8/68 |

OTHER PUBLICATIONS

Search Report dated Sep. 10, 2015 for European Application No. 15 15 9564.

* cited by examiner

*Primary Examiner* — Porfirio Nazario Gonzalez
*Assistant Examiner* — Kofi Adzamli
(74) *Attorney, Agent, or Firm* — Birch, Stewart, Kolasch & Birch, LLP

(57) ABSTRACT

A silazane compound useful as synthesis intermediates for paint additives, polymer modifiers, pharmaceuticals and agricultural chemicals is efficiently prepared by reaction of a halosilane compound with an amino-containing compound in a solvent which is the same silazane compound as the target product.

2 Claims, No Drawings

PREPARATION OF SILAZANE COMPOUND

CROSS-REFERENCE TO RELATED APPLICATION

This non-provisional application claims priority under 35 U.S.C. §119(a) on Patent Application No. 2014-076769 filed in Japan on Apr. 3, 2014, the entire contents of which are hereby incorporated by reference.

TECHNICAL FIELD

This invention relates to a method for preparing silazane compounds which are useful as synthesis intermediates for paint additives, polymer modifiers, pharmaceuticals, and agricultural chemicals.

BACKGROUND ART

Silazane compounds are useful as intermediates for the synthesis of paint additives, polymer modifiers, pharmaceuticals, and agricultural chemicals.

As is well known in the art, silazane compounds are prepared by reaction of a halosilane compound with an amino-containing compound. In this reaction, not only the target silazane compound, but also a hydrogen halide by-product forms. The hydrogen halide reacts with the amino-containing compound to form a hydrogen halide salt of the amino-containing compound in stoichiometric amount. The resulting hydrogen halide salt of the amino-containing compound is normally solid, does not dissolve in the reaction system, and precipitates out during the reaction. The precipitates turn the reaction solution into a slurry, interfering with stirring. Generally, a solvent is added to continue stirring during the reaction. For example, U.S. Pat. No. 2,429,883 discloses a method for preparing silazane compounds using diethylether or benzene as a solvent.

CITATION LIST

Patent Document 1: U.S. Pat. No. 2,429,883

DISCLOSURE OF INVENTION

However, a large amount of solvent is required to continue stirring. The solvent must be distilled off when the target silazane compound is isolated by distillation. These procedures are cumbersome. Accordingly, there is a need for a more efficient method for preparing silazane compounds.

An object of the invention is to provide a method for efficiently preparing silazane compounds.

The inventors have found that a silazane compound is efficiently prepared by reaction of a halosilane compound with an amino-containing compound when a silazane compound which is the same as the target product is used as a solvent. When the same silazane compound as the target product is used as a solvent, the resulting slurry which contains a hydrogen halide salt of the amino-containing compound is improved in fluidity. The amount of the solvent used is reduced. Since the solvent is the silazane compound, the step of fractional distillation of the solvent is unnecessary.

According to the invention, there is provided a method for preparing a silazane compound, comprising the step of reacting a halosilane compound having the general formula (1):

(1)

wherein $R^1$ is each independently hydrogen or a substituted or unsubstituted monovalent hydrocarbon group of 1 to 20 carbon atoms, X is a halogen atom, n is an integer of 0 to 3, and $R^1$ groups bond together to form a $C_2$-$C_{20}$ ring with the silicon atom to which they are attached when n is 2 or 3, with an amino-containing compound having the general formula (2):

(2)

wherein $R^2$ and $R^3$ are independently hydrogen or a substituted or unsubstituted monovalent hydrocarbon group of 1 to 20 carbon atoms, or the general formula (3):

(3)

wherein $R^4$ is a divalent organic group of 1 to 20 carbon atoms which may contain a heteroatom, in a solvent which is the same silazane compound as the target product.

In a preferred embodiment, the silazane compound has the general formula (4), (5), (6) or (7).

(4)

Herein $R^1$, $R^2$, $R^3$ and n are as defined above.

(5)

Herein $R^1$, $R^4$ and n are as defined above.

(6)

Herein $R^1$ and $R^3$ are as defined above, and n is 3.

(7)

Herein $R^1$ and $R^3$ are as defined above, a is an integer of 2 to 20, and n is 2.

In a preferred embodiment, $R^2$ and $R^3$ in formula (2) are independently a substituted or unsubstituted monovalent hydrocarbon group of 1 to 20 carbon atoms.

A hydrogen halide salt of the amino-containing compound forms during the reaction. In a preferred embodiment, an alkaline aqueous solution is added to the reaction solution to dissolve the hydrogen halide salt of the amino-containing compound in the alkaline aqueous solution, thereby separating the amino-containing compound from an organic layer containing the silazane compound.

Advantageous Effects of Invention

According to the invention, silazane compounds can be efficiently prepared, which are useful as synthesis intermediates for paint additives, polymer modifiers, pharmaceuticals and agricultural chemicals.

DESCRIPTION OF PREFERRED EMBODIMENTS

One embodiment of the invention is a method for preparing a silazane compound by reaction of a halosilane compound having the general formula (1):

$$R^1{}_n SiX_{(4-n)} \quad (1)$$

wherein $R^1$ is each independently hydrogen or a substituted or unsubstituted monovalent hydrocarbon group of 1 to 20 carbon atoms, X is a halogen atom, n is an integer of 0 to 3, and $R^1$ groups bond together to form a $C_2$-$C_{20}$ ring with the silicon atom to which they are attached when n is 2 or 3, with an amino-containing compound having the general formula (2) or (3):

$$R^2 R^3 NH \quad (2)$$

wherein $R^2$ and $R^3$ are independently hydrogen or a substituted or unsubstituted monovalent hydrocarbon group of 1 to 20 carbon atoms,

(3)

wherein $R^4$ is a divalent organic group of 1 to 20 carbon atoms which may contain a heteroatom. In the reaction, a silazane compound which is the same as the target product is used as a solvent.

In formulae (1) and (2), $R^1$ to $R^3$ are each independently hydrogen or a substituted or unsubstituted monovalent hydrocarbon group of 1 to 20 carbon atoms, preferably 1 to 10 carbon atoms, more preferably 1 to 5 carbon atoms, which includes straight, branched or cyclic alkyl, alkenyl, aryl, and aralkyl groups. Examples include straight alkyl groups such as methyl, ethyl, propyl, butyl, pentyl, hexyl, heptyl, octyl, decyl, dodecyl, tetradecyl, hexadecyl, octadecyl and eicosyl, branched alkyl groups such as isopropyl, isobutyl, sec-butyl, tert-butyl, thexyl and 2-ethylhexyl, cyclic alkyl groups such as cyclopentyl and cyclohexyl, alkenyl groups such as vinyl, allyl and propenyl, aryl groups such as phenyl and tolyl, and aralkyl groups such as benzyl, with methyl, ethyl, isopropyl, sec-butyl and tert-butyl being preferred. The substituted forms of the foregoing groups in which some or all hydrogen atoms are substituted are also acceptable. Suitable substituents on the foregoing groups include alkoxy groups such as methoxy, ethoxy and (iso)propoxy, halogen atoms such as fluorine, chlorine, bromine and iodine, cyano groups, amino groups, acyl groups of 2 to 10 carbon atoms, trichlorosilyl groups, and trialkylsilyl, dialkylmonochlorosilyl, monoalkyldichlorosilyl, trialkoxysilyl, dialkylmonoalkoxysilyl and monoalkyldialkoxysilyl groups wherein each alkyl or alkoxy moiety has 1 to 5 carbon atoms.

In formula (3), $R^4$ is a divalent organic group of 1 to 20 carbon atoms which may contain a heteroatom, examples of which include alkylene groups such as methylene, ethylene, methylethylene, propylene, methylpropylene, tetramethylene, hexamethylene, octamethylene, decamethylene and isobutylene, arylene groups such as phenylene, aralkylene groups such as methylenephenylene and methylenephenylenemethylene, and alkylene groups containing a heteroatom (e.g., oxygen and nitrogen), such as 3-oxapentylene, 3-azapentylene and 3-methy-3-azapentylene.

In formula (1), the halogen atom is selected from fluorine, chlorine, bromine, and iodine.

Examples of the halosilane compound of formula (1) include dimethylchlorosilane, trimethylchlorosilane, diethylchlorosilane, ethyldimethylchlorosilane, diethylmethylchlorosilane, triethylchlorosilane, vinyldimethylchlorosilane, tripropylchlorosilane, triisopropylchlorosilane, tributylchlorosilane, tert-butyldimethylchlorosilane, di-tert-butylmethylchlorosilane, tri-tert-butylchlorosilane, triisobutylchlorosilane, tri-sec-butylchlorosilane, hexyldimethylchlorosilane, thexyldimethylchlorosilane, octyldimethylchlorosilane, decyldimethylchlorosilane, octadecyldimethylchlorosilane, cyclopentyldimethylchlorosilane, cyclohexyldimethylchlorosilane, tricyclopentylchlorosilane, tricyclohexylchlorosilane, dimethylphenylchlorosilane, methyldiphenylchlorosilane, triphenylchlorosilane, tert-butyldiphenylchlorosilane, di-tert-butylphenylchlorosilane, styryldimethylchlorosilane, 2-cyanoethyldimethylchlorosilane, acetoxypropyldimethylchlorosilane, 3-acryloxypropyldimethylchlorosilane, 3-methacryloxypropyldimethylchlorosilane, chloromethyldimethylchlorosilane, 3-chloropropyldimethylchlorosilane, 3,3,3-trifluoropropyldimethylchlorosilane, 3,3,4,4,5,5,6,6,6-nonafluorohexyldimethylchlorosilane, 3,3,4,4,5,5,6,6,7,7,8,8,9,9,10,10,10-heptadecafluorodecyldimethylchlorosilane, dichlorosilane, methyldichlorosilane, dimethyldichlorosilane, ethyldichlorosilane, diethyldichlorosilane, vinylmethyldichiorosilane, divinyldichlorosilane, propylmethyldichiorosilane, dibutyldichlorosilane, tert-butylmethyldichlorosilane, di-tert-butyldichlorosilane, diisobutyldichlorosilane, di-sec-butyldichlorosilane, hexylmethyldichlorosilane, thexylmethyldichiorosilane, octylmethyldichlorosilane, decylmethyldichlorosilane, octadecylmethyldichiorosilane, cyclopentylmethyldichlorosilane, cyclohexylmethyldichlorosilane, dicyclopentyldichlorosilane, dicyclohexyldichlorosilane, methylphenyldichlorosilane, diphenyldichlorosilane, tert-butylphenyldichlorosilane, styrylmethyldichlorosilane, 2-cyanoethylmethyldichlorosilane, acetoxypropylmethyldichlorosilane, 3-acryloxypropylmethyldichlorosilane, 3-methacryloxypropylmethyldichlorosilane, chloromethylmethyldichlorosilane, 3-chloropropylmethyldichlorosilane, 3,3,3-trifluoropropylmethyldichlorosilane, 3,3,4,4,5,5,6,6,6-nonafluorohexylmethyldichiorosilane, 3,3,4,4,5,5,6,6,7,7,8,8,9,9,10,10,10-heptadecafluorodecylmethyldichlorosilane, trichlorosilane, methyltrichlorosilane, ethyltrichlorosilane, vinyltrichlorosilane, propyltrichlorosilane, isopropyltrichlorosilane, butyltrichlorosilane, tert-butyltrichlorosilane, isobutyltrichlorosilane, sec-butyltrichlorosilane, hexyltrichlorosilane, thexyltrichlorosilane, octyltrichlorosilane, decyltrichlorosilane, octadecyltrichlorosilane, cyclopentyltrichlorosilane, cyclohexyltrichlorosilane, phenyltrichlorosilane, styryltrichlorosilane, 2-cyanoethyltrichlorosilane, acetoxypropyltrichlorosilane, 3-acryloxypropyltrichlorosilane, 3-methacryloxypropyltrichlorosilane, chloromethyltrichlorosilane, 3-chloropropyltrichlorosilane, 3,3,3-trifluoropropyltrichlorosilane, 3,3,4,4,5,5,6,6,6-nonafluorohexyltrichlorosilane, 3,3,4,4,5,5,6,6,7,7,8,8,9,9,10,10,10-heptadecafluorodecyltrichlorosilane, tetrachlorosilane, 1,2-bis(dimethylchlorosilyl)ethane, 1,2-bis(methyldichlorosilyl)ethane, 1,2-bis(trichlorosilyl)ethane, 1,6-bis(dimethylchlorosilyl)hexane, 1,6-(methyldichlorosilyl)hexane, 1,6-bis(trichlorosilyl)hexane, bis(dimethylchlorosilyl)norbornane, bis(methyldichlorosilyl)norbornane, bis(trichlorosilyl)norbornane, dimethylbromosilane, trimethylbromosilane, diethylbromosilane, ethyldimethylbromosilane, diethylmethylbromosilane, triethylbromosilane, vinyldimethylbromosilane, tripropylbromosilane, triisopropylbromosilane, tributylbromosilane, tert-butyldimethylbromosilane, di-tert-butylmethylbromosilane, tri-tert-butylbromosilane, triisobutylbromosilane, tri-sec-butylbromosilane, hexyldimethylbromosilane, thexyldimethylbromosilane, octyldimethylbromosilane, decyldimethylbromosilane, octadecyldimethylbromosilane, cyclopentyldimethylbromosilane, cyclohexyldimethylbromosilane, tricyclopentylbromosilane, tricyclohexylbromosilane, dimethylphenylbromosilane, methyldiphenylbromosilane, triphenylbromosilane, tert-butyldiphenylbromosilane, di-tert-butylphenylbromosilane, styryldimethylbromosilane, 2-cyanoethyldimethylbromosilane, acetoxypropyldimethylbromosilane, 3-acryloxypropyldimethylbromosilane, 3-methacryloxypropyldimethylbromosilane, bromomethyldimethylbromosilane, 3-bromopropyldimethylbromosilane, 3,3,3-trifluoropropyldimethylbromosilane, 3,3,4,4,5,5,6,6,6-nonafluorohexyldimethylbromosilane, 3,3,4,4,5,5,6,6,7,7,8,8,9,9,10,10,10-heptadecafluorodecyldimethylbromosilane, dibromosilane, methyldibromosilane, dimethyldibromosilane, ethyldibromosilane, diethyldibromosilane, vinylmethyldibromosilane, divinyldibromosilane, propylmethyldibromosilane, dibutyldibromosilane, tert-butylmethyldibromosilane, di-tert-butyldibromosilane, diisobutyldibromosilane, di-sec-butyldibromosilane, hexylmethyldibromosilane, thexylmethyldibromosilane, octylmethyldibromosilane, decylmethyldibromosilane, octadecylmethyldibromosilane, cyclopentylmethyldibromosilane, cyclohexylmethyldibromosilane, dicyclopentyldibromosilane, dicyclohexyldibromosilane, methylphenyldibromosilane, diphenyldibromosilane, tert-butylphenyldibromosilane, styrylmethyldibromosilane, 2-cyanoethylmethyldibromosilane, acetoxypropylmethyldibromosilane, 3-acryloxypropylmethyldibromosilane, 3-methacryloxypropylmethyldibromosilane, bromomethylmethyldibromosilane, 3-bromopropylmethyldibromosilane, 3,3,3-trifluoropropylmethyldibromosilane, 3,3,4,4,5,5,6,6,6-nonafluorohexylmethyldibromosilane, 3,3,4,4,5,5,6,6,7,7,8,8,9,9,10,10,10-heptadecafluorodecylmethyldibromosilane, tribromosilane, methyltribromosilane, ethyltribromosilane, vinyltribromosilane, propyltribromosilane, isopropyltribromosilane, butyltribromosilane, tert-butyltribromosilane, isobutyltribromosilane, sec-butyltribromosilane, hexyltribromosilane, thexyltribromosilane, octyltribromosilane, decyltribromosilane, octadecyltribromosilane, cyclopentyltribromosilane, cyclohexyltribromosilane, phenyltribromosilane, styryltribromosilane, 2-cyanoethyltribromosilane, acetoxypropyltribromosilane, 3-acryloxypropyltribromosilane, 3-methacryloxypropyltribromosilane, bromomethyltribromosilane, 3-bromopropyltribromosilane, 3,3,3-trifluoropropyltribromosilane, 3,3,4,4,5,5,6,6,6-nonafluorohexyltribromosilane, 3,3,4,4,5,5,6,6,7,7,8,8,9,9,10,10,10-heptadecafluorodecyltribromosilane, tetrabromosilane, 1,2-bis(dimethylbromosilyl)ethane, 1,2-bis(methyldibromosilyl)ethane, 1,2-bis(tribromosilyl)ethane, 1,6-bis(dimethylbromosilyl)hexane, 1,6-(methyldibromosilyl)hexane, 1,6-bis(tribromosilyl)hexane, bis(dimethylbromosilyl)norbornane, bis(methyldibromosilyl)norbornane, and bis(tribromosilyl)norbornane.

Examples of the amino-containing compound of formula (2) include ammonia, methylamine, ethylamine, propylamine, isopropylamine, allylamine, butylamine, pentylamine, hexylamine, octylamine, 2-ethylhexylamine, benzylamine, cyclopentylamine, cyclohexylamine, ethylenediamine, diethylenetriamine, triethylenetetramine, 1,6-diaminohexane, aniline, toluidine, xylidine, naphthylamine, xylylenediamine, dimethylamine, diethylamine, dipropylamine, diisopropylamine, diallylamine, dibutylamine, dipentylamine, dioctylamine, di(2-ethylhexyl)amine, N-methylaniline, and diphenylamine.

Examples of the amino-containing compound of formula (3) include ethyleneimine, pyrrolidine, piperidine, pipecoline, piperazine, N-methylpiperazine, N-ethylpiperazine, morpholine, imidazole, triazole, and indole.

Preferably the silazane compound which is the target product and also serves as a solvent for the relevant reaction has the general formula (4), (5), (6) or (7).

$$R^1{}_n Si(NR^2R^3)_{(4-n)} \quad (4)$$

Herein $R^1$, $R^2$, $R^3$ and n are as defined above.

Herein $R^1$, $R^4$ and n are as defined above.

Herein $R^1$ and $R^3$ are as defined above, and n is 3.

Herein $R^1$ and $R^3$ are as defined above, a is an integer of 2 to 20, preferably 3 to 10, more preferably 3 to 5, and n is 2.

The amount of the halosilane compound used is not particularly limited. From the aspects of reactivity and productivity, the halosilane compound is preferably used in an amount to give 0.1 to 4.0 moles, more preferably 0.2 to 3.0 moles of silicon-halogen bond per mole of the reactive N—H bond of the amino-containing compound.

In the reaction of a halosilane compound of formula (1) with an amino-containing compound of formula (2) or (3) to form a silazane compound, the same silazane compound as the reaction product is used as a solvent.

The silazane compound used as solvent may be the compound purified by removal of salt from and/or distillation of the synthetic reaction solution. From the aspect of quality of the final silazane compound, the silazane compound purified by distillation is preferably used.

The amount of the silazane compound used as a solvent is not particularly limited. From the aspects of reactivity and productivity, the silazane compound is preferably used in an amount of 0.1 to 10 moles, more preferably 0.5 to 5 moles per mole of the reactive N—H bond of the amino-containing compound.

In the silylation reaction of the amino-containing compound, a hydrogen halide forms as by-product. The hydrogen halide may be trapped using the amino-containing compound of formula (2) or (3) itself or another amine as a base. Suitable other amine compounds include trimethylamine, triethylamine, tripropylamine, tributylamine, ethyldiisopropylamine, pyridine, dimethylaminopyridine, dimethylaniline, methylimidazole, tetramethylethylenediamine and 1,8-diazabicyclo[5.4.0]undecene-7.

The amount of the other amine compound used is not particularly limited. From the aspects of reactivity and productivity, the other amine compound is preferably used in an amount of 0.3 to 10.0 moles, more preferably 0.5 to 5.0 moles per mole of the reactive N—H bond of the amino-containing compound.

Although the reaction takes place even in a catalyst-free system, a catalyst may be added for the purpose of promoting the kinetics of reaction. Examples of the catalyst include sulfuric acid, sulfonic acid derivatives such as methanesulfonic acid, benzenesulfonic acid, toluenesulfonic acid, dodecylbenzenesulfonic acid and trifluoromethanesulfonic acid, hydrochloric acid, nitric acid, and salts of these acids. The amount of the catalyst used is not particularly limited. From the aspects of reactivity and productivity, the catalyst is preferably used in an amount of 0.0001 to 0.1 mole, more preferably 0.001 to 0.05 mole per mole of the reactive N—H bond of the amino-containing compound.

The reaction temperature is preferably 0° C. to 200° C., more preferably 10° C. to 180° C., though not limited thereto.

A solvent other than the silazane compound may be further added as long as this does not compromise the objects of the invention. Examples of the solvent include hydrocarbon solvents such as pentane, hexane, cyclohexane, heptane, isooctane, benzene, toluene and xylene, ether solvents such as diethyl ether, tetrahydrofuran and dioxane, ester solvents such as ethyl acetate and butyl acetate, aprotic polar solvents such as acetonitrile and N,N-dimethylformamide, and chlorinated hydrocarbon solvents such as dichloromethane and chloroform. These solvents may be used alone or in admixture of two or more. The solvent is preferably used in an amount of 0.1 to 10 moles, more preferably 0.5 to 2 moles per mole of the silazane compound as solvent.

At the end of reaction, the amino-containing compound forms a hydrogen halide (typically hydrochloride) salt, which may be removed by any suitable techniques such as filtration of the reaction solution, and addition of water or an alkaline aqueous solution such as sodium hydroxide or potassium hydroxide aqueous solution and subsequent separation. In the latter technique of adding an alkaline aqueous solution to the reaction solution, the amino-containing compound is liberated from the hydrogen halide salt of amino-containing compound, so that the amino-containing compound may be recovered. In this sense, the technique of adding an alkaline aqueous solution is preferred.

After the salt is removed from the reaction solution as mentioned above, the target product may be collected from the reaction solution using conventional techniques such as distillation.

EXAMPLE

Examples are given below by way of illustration and not by way of limitation.

Example 1

A flask equipped with a stirrer, reflux condenser, dropping funnel and thermometer was charged with 103.3 g (0.8 mole) of dimethyldichlorosilane, 200 g (0.99 mole) of bis(diethylamino)dimethylsilane as a solvent, and 0.38 g (0.004 mole) of methanesulfonic acid, and heated at 60° C. Once the internal temperature became steady, 245.6 g (3.4 moles) of diethylamine was added dropwise over 3 hours. The contents were stirred at the temperature for 1 hour. The reaction solution was cooled to room temperature, after which 400 g of 20 wt % sodium hydroxide aqueous solution was added. The organic layer was separated and distilled, collecting bis(diethylamino)dimethylsilane as a fraction at a boiling point of 78° C./2.0 kPa. Amount 336.7 g, yield 84% (based on the weight of dimethyldichlorosilane). The yield of bis(diethylamino)dimethylsilane which was calculated based on the maximum weight of flask contents (i.e., the total weight of flask contents with 20 wt % sodium hydroxide aqueous solution added) was 144.0 g per kg of the maximum weight of flask contents.

Comparative Example 1

Reaction was performed as in Example 1 except that the solvent was changed to 200 g of toluene. A salt formed during dropwise addition of diethylamine, to inhibit stirring. It was necessary to add another 200 g of toluene. The reaction solution was cooled to room temperature, after which 400 g of 20 wt % sodium hydroxide aqueous solution was added. The organic layer was separated, from which toluene was distilled off. By further distillation, bis(diethylamino)dimethylsilane was collected as a fraction at a boiling point of 78° C./2.0 kPa. Amount 133.9 g, yield 83% (based on the weight of dimethyldichlorosilane). The yield of bis(diethylamino)dimethylsilane which was calculated based on the maximum weight of flask contents (i.e., the total weight of flask contents with 20 wt % sodium hydroxide aqueous solution added) was 116.5 g per kg of the maximum weight of flask contents. Comparative Example 1 was less productive than Example 1.

Example 2

A flask equipped with a stirrer, reflux condenser, dropping funnel and thermometer was charged with 152.9 g (0.8 mole) of methylphenyldichlorosilane, 150 g (0.57 mole) of bis(diethylamino)methylphenylsilane as a solvent, and 0.38 g (0.004 mole) of methanesulfonic acid, and heated at 60° C. Once the internal temperature became steady, 245.6 g (3.4 moles) of diethylamine was added dropwise over 3 hours. The contents were stirred at the temperature for 1 hour. The reaction solution was cooled to room temperature, after which 400 g of 20 wt % sodium hydroxide aqueous solution was added. The organic layer was separated and distilled, collecting bis(diethylamino)methylphenylsilane as a fraction at a boiling point of 126° C./0.4 kPa. Amount 325.9 g, yield 83% (based on the weight of methylphenyldichlorosilane).

Comparative Example 2

Reaction was performed as in Example 2 except that the solvent was changed to 150 g of xylene. A salt formed during dropwise addition of diethylamine, to inhibit stirring. It was necessary to add another 180 g of xylene. The reaction solution was cooled to room temperature, after which 400 g of 20 wt % sodium hydroxide aqueous solution was added. The organic layer was separated, from which xylene was distilled off. By further distillation, bis(diethylamino)methylphenylsilane was collected as a fraction at a boiling point of 82° C./1.0 kPa. Amount 174.0 g, yield 82% (based on the weight of methylphenyldichlorosilane).

Example 3

A flask equipped with a stirrer, reflux condenser, dropping funnel and thermometer was charged with 112.9 g (0.8 mole)

of methylvinyldichlorosilane, 200 g (0.93 mole) of bis(diethylamino)methylvinylsilane as a solvent, and 0.38 g (0.004 mole) of methanesulfonic acid, and heated at 60° C. Once the internal temperature became steady, 245.6 g (3.4 moles) of diethylamine was added dropwise over 3 hours. The contents were stirred at the temperature for 1 hour. The reaction solution was cooled to room temperature, after which 400 g of 20 wt % sodium hydroxide aqueous solution was added. The organic layer was separated and distilled, collecting bis(diethylamino)methylvinylsilane as a fraction at a boiling point of 82° C./1.0 kPa. Amount 344.7 g, yield 83% (based on the weight of methylvinyldichlorosilane).

Comparative Example 3

Reaction was performed as in Example 3 except that the solvent was changed to 200 g of toluene. A salt formed during dropwise addition of diethylamine, to inhibit stirring. It was necessary to add another 200 g of toluene. The reaction solution was cooled to room temperature, after which 400 g of 20 wt % sodium hydroxide aqueous solution was added. The organic layer was separated, from which toluene was distilled off. By further distillation, bis(diethylamino)methylvinylsilane was collected as a fraction at a boiling point of 82° C./1.0 kPa. Amount 140.4 g, yield 82% (based on the weight of methylvinyldichlorosilane).

Example 4

A flask equipped with a stirrer, reflux condenser, dropping funnel and thermometer was charged with 120.6 g (0.8 mole) of triethylchlorosilane, 100 g (0.41 mole) of dibutylaminotriethylsilane as a solvent, and 0.38 g (0.004 mole) of methanesulfonic acid, and heated at 60° C. Once the internal temperature became steady, 217.0 g (1.7 moles) of dibutylamine was added dropwise over 3 hours. The contents were stirred at the temperature for 1 hour. The reaction solution was cooled to room temperature, after which 200 g of 20 wt % sodium hydroxide aqueous solution was added. The organic layer was separated and distilled, collecting dibutylaminotriethylsilane as a fraction at a boiling point of 86° C./0.4 kPa. Amount 304.5 g, yield 84% (based on the weight of triethylchlorosilane).

Comparative Example 4

Reaction was performed as in Example 4 except that the solvent was changed to 100 g of hexane. A salt formed during dropwise addition of dibutylamine, to inhibit stirring. It was necessary to add another 100 g of hexane. The reaction solution was cooled to room temperature, after which 200 g of 20 wt % sodium hydroxide aqueous solution was added. The organic layer was separated, from which hexane was distilled off. By further distillation, dibutylaminotriethylsilane was collected as a fraction at a boiling point of 86° C./0.4 kPa. Amount 161.1 g, yield 83% (based on the weight of triethylchlorosilane).

Japanese Patent Application No. 2014-076769 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing a silazane compound, target product of formula (4) or of formula (5)

$$R^1{}_n Si(NR^2R^3)_{(4-n)} \tag{4}$$

wherein each $R^1$ is independently hydrogen or a substituted or unsubstituted monovalent hydrocarbon group of 1 to 20 carbon atoms, $R^2$ and $R^3$ are independently a substituted or unsubstituted monovalent hydrocarbon group of 1 to 20 carbon atoms, n is an integer of 0 to 3, and $R^1$ groups bond together to form a $C_2$-$C_{20}$ ring with the silicon atom to which they are attached when n is 2 or 3,

wherein each $R^1$ is independently hydrogen or a substituted or unsubstituted monovalent hydrogen group of 1 to 20 carbon atoms, $R^4$ is a divalent organic group of 1 to 20 carbon atoms which may contain a heteroatom, and n is an integer of 0 to 3, said method comprising the step of reacting a halosilane compound having the general formula (1):

$$R^1{}_n SiX_{(4-n)} \tag{1}$$

wherein X is a halogen atom and $R^1$ and n are as defined above, with an amino-containing compound having the general formula (2):

$$R^2R^3NH \tag{2}$$

wherein $R^2$ and $R^3$ are as defined above or with an amino-containing compound having the general formula (3):

wherein $R^4$ is as defined above in a solvent which is the same silazane compound as the target product.

2. The method of claim 1, wherein a hydrogen halide salt of the amino-containing compound forms during the reaction, the method further comprising the step of adding an alkaline aqueous solution to the reaction solution to dissolve the hydrogen halide salt of the amino-containing compound in the alkaline aqueous solution, thereby separating the amino-containing compound from an organic layer containing the silazane compound.

* * * * *